United States Patent [19]

Noll

[11] Patent Number: 4,514,499

[45] Date of Patent: Apr. 30, 1985

[54] CELL CULTURE USING A MONOLITHIC SUPPORT

[75] Inventor: Lee A. Noll, Horseheads, N.Y.

[73] Assignee: Corning Glass Works, Corning, N.Y.

[21] Appl. No.: 464,040

[22] Filed: Feb. 4, 1983

[51] Int. Cl.³ .............................................. C12N 5/00
[52] U.S. Cl. ..................................... 435/240; 435/284
[58] Field of Search ............... 435/240, 241, 284, 285, 435/286, 182

[56] References Cited

U.S. PATENT DOCUMENTS

| | | |
|---|---|---|
| 3,732,149 | 5/1973 | Santero . |
| 3,827,943 | 8/1974 | Mann . |
| 3,853,712 | 12/1974 | House et al. . |
| 3,883,393 | 5/1975 | Knazek et al. . |
| 3,948,732 | 4/1976 | Haddad et al. ..................... 435/285 |
| 4,075,092 | 2/1978 | White et al. . |
| 4,317,886 | 3/1982 | Johnson et al. . |
| 4,440,853 | 4/1984 | Michaels et al. ..................... 435/182 |

OTHER PUBLICATIONS

Benoit et al., Biotechnology and Bioengineering, vol. XVII, pp. 1617–1626, (1975); An Evaluation of a Ceramic Monolith as an Enzyme Support Material.

T. Cartwright and J. R. Birch, Tissue Culture–A Review–Process Biochemistry, Mar. 1978.

Charles Ghommidh, Utilisation de Microorganismes Immobilises en Reacteur Aere; These;.

Ghommidh et al.; A Study of Acetic Acid Production by Immobilized Acetobacter Cells: Oxygen Transfer; Biotechnology and Bioengineering, vol. XXIV, pp. 605–617; (1982).

Girard et al.; Monolayer Cultures of Animal Cells with the Gyrogen Equipped with Tubes; Biotechnology and Bioengineering, vol. XXII, pp. 477–493, (1980).

Large Scale Perfusion Culture of Cells Growing on Surfaces with Automatic Gas and Medium Control—Dr. Erik Harms, Cytobiologie, European Journal of Cell Biology, 18.67–75, (1978).

Mona D. Jensen; Production of Anchorage–Dependent Cells–Problems and Their Possible Solutions; Biotechnology and Bioengineering: vol. XXIII, pp. 2703–2716, (1981).

Kan et al., Urocanic Acid Production Using Whole Cells Immobilized in a Hollow Fiber Reactor; Biotechnology and Bioengineering, vol. XX, pp.217–230, (1978).

Keay et al., Recent Advances in the Technology of Animal Cell Production; Process Biochemistry, Mar. 1979.

Primary Examiner—Sam Rosen
Attorney, Agent, or Firm—B. D. Voyce; W. E. Maycock

[57] ABSTRACT

A novel immobilized cell composite used in a novel apparatus/method for cell culture. The composite comprises:

(a) a high surface area monolithic support having a multiplicity of mutually parallel channels passing therethrough, the channels having walls formed of a medium-insoluble, non-toxic, composition and the support having at least about 20 channels per square inch of cross-sectional area; and (b) a population of plant or animal tissue cells anchored to the porous channel walls.

18 Claims, 12 Drawing Figures

CELL CULTURE USING A MONOLITHIC SUPPORT

TECHNICAL FIELD

The present invention relates to cell culture. More particularly, the present invention relates to a mass tissue cell culture apparatus/process and an immobilized cell composite which are especially useful in the culturing of anchorable animal and plant cells.

BACKGROUND ART

As used herein, tissue culture refers to the process by which tissue cells are grown in vitro, i.e., in artificial media under relatively controlled conditions.

In general, tissue cells are grown either in suspension or attached to a solid support. Some cells do not need a solid support and can also grow in a suspended condition. However, other cells grow only when attached to a surface, i.e., anchorage-dependent cells. The term anchorable cells is used herein to include both types of cells.

At the present time, perhaps the most common large scale tissue culture procedure involves the use of multiple roller bottles. As noted by Jensen, Biotechnol. Bioeng., 23, 2703 (1981), roller bottle culturing is extremely expensive, requiring intensive labor and considerable capital outlay for incubation equipment. Another disadvantage is an increased risk of contamination because the roller bottle procedure is essentially a batch process involving hundreds of separate manipulations.

Many recent innovations have been directed to overcoming these drawbacks. Examples of such innovations include, by way of illustration only, microcarrier beads, artificial capillaries (hollow fibers), and bundled tubes. Indeed, some efforts have been directed to improving roller bottles themselves.

U.S. Pat. No. 4,317,886 discloses a roller bottle comprising an outer housing defining a hollow chamber therein, with at least one annular member placed inside the chamber spaced a short radial distance inwardly from the outer housing. In effect, the disclosed roller bottle is equivalent to a series of increasingly smaller roller bottles located within a single housing.

Another way to increase the surface area in a conventional roller bottle is disclosed in U.S. Pat. No. 3,853,712. Here, a flexible strip is wound or otherwise formed by successive changes of direction into a compact cell support which can fit inside a roller bottle. As an example, a length of corrugated strip material and a length of smooth, planar strip material were wound together into a self-spacing spiral.

While the use of microcarriers for culturing mammalian anchorage-dependent cells in suspension has been given increasing attention in recent years, such use is not directly related to the present invention. Microcarrier culture systems are based on suspending literally millions of individual, minute beads, not monolithic supports.

Of more immediate interest is the use of a plurality of tubes for growing anchorable cells. By way of illustration, U.S. Pat. No. 3,732,149 discloses an apparatus which comprises a plurality of mutually parallel columns having a uniform length. These columns are clamped together at the ends by manifolds which are fixed onto a shaft which is parallel to the columns. In use, the cells grow on the inner surfaces of the columns, through which media is pumped. The entire device is rotated about the shaft. In effect, the disclosed apparatus is a variation of the roller bottle technique.

A somewhat similar device also is disclosed in U.S. Pat. No. 3,827,943. Here individual tubes having an internal diameter of from 1 to 10 cm have a single inlet/outlet tube. This feature allegedly reduces the risk of infection.

Another variation of the bundled tube concept is the Gyrogen. While similar in configuration to the two devices discussed above, it differs in that media is circulated both through and around the tubes. Thus, cells are able to attach on both the internal and external surfaces of the tubes. As with the preceding bundled tube devices, the entire apparatus is rotated about a central axis. See, e.g., H. C. Girard et al., Biotechnol. Bioeng., 22, 477 (1980).

It should be noted that the bundled tube process and variations thereof, should not be confused with the artificial capillary or hollow fiber concept. They are distinct. In the artificial capillary process, the cells and medium do not mix. For example, the cells attach to the outer surfaces of the capillaries, while the nutrient medium flows through the capillaries. Nutrient substances diffuse through the capillary walls and into the cells, while cell products or metabolites diffuse from the cells through the capillary wall into the medium. See U.S. Pat. No. 3,883,393; J. K. Kan et al., Biotechnol. Bioeng., 20, 217 (1978); and U.S. Pat. No. 4,075,092.

Another means of increasing the surface area to volume ratio of a culture vessel is to pack the culture vessel with bits of inert material. One disclosure states that a double-walled cylindrical glass vessel can be filled with segments of glass tubing of about 6 mm in length to increase the surface area. The reaction vessel was part of an instrument or apparatus having automatic gas and medium control. See, E. Harms et al., Cytobiologie, 18, 67 (1978).

For recent summaries of tissue culture in general, see T. Cartwright et al., Process Biochemistry, 13, 3 (1978); L. Keay et al., Process Biochemistry, 14, 17 (1979); and M. D. Jensen, supra.

Finally, an embodiment of the supports useful in the preparation of the present immobilized animal or plant cell composite has been described as a support for enzymes and microbes. Specifically, M. R. Benoit et al., Biotechnol. Bioeng., 27 1617 (1975), describes the immobilization of catalase on commercially available monolithic catalyst supports. The enzyme was covalently coupled to the support by means of an intermediate silane coupling agent activated with glutaraldehyde.

As a microbial support, a monolithic substrate was used in a study of acetic acid production by immobilized Acetobacter aceti cells. These cells were allowed to attach to a ceramic support, cordierite, by adsorption. See C. Ghommidh et al., Biotechnol. Bioeng., 24, 605 (1982), a reference appears to be based, at least in part, upon a thesis by C. Ghommidh, which was published in 1980.

DISCLOSURE OF THE INVENTION

In accordance with the present invention, an immobilized cell composite is characterized by a high surface area support having a population of animal or plant cells attached to the surface thereof. The support is medium-insoluble and non-toxic to the cells. The support structure is essentially a honeycombed monolith. Inlet and outlet faces allow liquid to flow through channels in the monolith to provide nutrients to the anchored cells. The channels are substantially parallel to the direction of the flow.

A preferred embodiment discloses an immobilized cell composite characterized by a high surface area to volume support having a population of animal or plant cells attached to the surface wherein the monolithic structure comprises a matrix of thin porous walls. A plurality of passageways are defined by these walls. They extend longitudinally and mutually parallel through the monolith and between inlet and outlet faces of such structure. The dimensions of these passageways are at least about 20 passageways per square inch (about 3 passageways per square centimeter) of structure cross-sectional area.

It is an object of the present invention to provide a mass cell culture apparatus/process which uses an immobilized cell composite to either grow cells only for harvesting or for useful products obtainable from cell cultures; e.g., metabolites, enzymes.

It also is an object of the present invention to provide an immobilized cell composite comprising a high surface area support having a population of animal or plant cells bonded to the surface thereof.

These and other objects will be readily apparent to one having ordinary skill in the art from a consideration of the specification and claims which follow.

The present invention also discloses a particularly efficient method for culturing anchorable plant or animal tissue cells using a novel immobilized cell composite. A dense population of cells anchored to support surfaces with a high surface area to volume reactor is cultured by means of a flowing nutrient medium. The nutrient medium is continuously conditioned to provide a controlled environment for the cells. The flow direction is substantially parallel to the support surfaces in the reactor.

The immobilized cell composite is characterized by a monolithic honeycomb structure having a multiplicity of mutually parallel channels. The channel walls are formed of a medium-insoluble, non-toxic porous inorganic composition which may vary considerably. This whole assembly is surrounded by a means which allows a laminar, nonturbulent flow to pass by the channel surfaces.

A typical support is a ceramic honeycomb structure composed of cordierite. It incorporates a multiplicity of straight, parallel channels of square cross-section, at a cross-sectional channel density in the range of about 100–1000 channels per square inch. This support is surrounded or encapsulated in such a manner that a laminar flow of liquids can pass through the channels.

Anchored to the channel walls of this support is a population of anchorable cells derived from plant or animal tissue, most preferably selected from but not being limited to the group comprising animal lymphocyte, epithelial or fibroblast cells.

In a process for culturing the cells in accordance with the invention, a known fluid medium suitable for cell culture is flowed over the seeded anchored cells. The flow rate is at least sufficient to provide the cells with the quantities of oxygen and nutrients necessary for cell sustenance and, if desired, for cell growth. Laminar flow of the culture medium through the channels facilitates a continuously ample supply of growth essentials and a continuous removal of metabolic products. Thus, relatively high population densities can be established on the porous wall surfaces of the support.

Preferably, the medium is recaptured after a pass over the monolith surfaces. It is recirculated after receiving a replenishment of necessary nutrients and gases to optimal growth levels. The monitoring and adjusting of these levels can be done automatically and continuously.

Higher and more efficient yields of cultured cells are obtained when the support has cells growing uniformly on all exposed surfaces. In order to achieve this growth, one must begin by uniformly distributing cells when seeding the monolith. The seeding methods of the present disclosure are able not only to achieve uniform seeding, but do so in a relatively simple, labor-saving manner.

Seeding begins by flooding the composite with a culture medium. After being positioned such that one orientation of channel walls is horizontal, in the one charge method the monolith is flooded with a cell growth medium containing animal serum, preferably about 5% and a uniform cell suspension made by known methods.

A period of settling follows the flooding. Gravity cause the cells to settle uniformly over the horizontal channel surfaces. After a rest period sufficient to permit the settled cells to anchor, typically fifteen minutes, the monolith composite is returned to a vertical position. Here, the uniform cell suspension is recirculated over the monolith for five minutes at fast flow rates, typically a linear flow of about 0.1 to 2.5 cm/sec.

The settling/recirculating cycle is performed for each orientation of the channel surfaces. In other words, a monolith having square cross-sectional channels must undergo four orientations in order to be uniformly seeded. Each time the monolith is rotated 90° in its horizontal axis. The result is that the composite is uniformly seeded without requiring additional cell suspension concentrate for each orientation.

It should be noted that an alternate seeding method, the multiple charge method, can be used which avoids the use of 5% animal serum in the inoculating solutions. The difference in this approach is that new additions of cell concentrate must be added to the system before each orientation. If desired, the multiple charge seeding method can be done with mediums having animal serum.

Once the cells are seeded, they must be presented with an environment that is optimal for either cell growth or maintenance, i.e., keeping a support saturated with healthy adsorbed cells. Nutrients, temperature, and gasses should be present in amounts sufficient for either growth or maintenance throughout the support. In addition, cell metabolites will be release into the medium and should be removed or neutralized whenever they would slow cellular growth.

Of course, one must know the present quantitative status of these qualitative growth parameters in order to know what conditions need to be changed how much. Thus, means for measuring these parameters should be provided in the present culture system. Preferably, probes and sensors should read out pH, glucose, dissolved oxygen and dissolved carbon dioxide levels of the medium both before it enters, and after it leaves the support.

A bonus can arise from this measuring means. Since nutrient consumption and metabolite output levels vary in a direct proportion with cell numbers, over a sufficient length of time the growth pattern or performance of a support can be determined. This is especially true where a number of past performance profiles have been developed. Thus, when a particular rate of change in parameters is reached, one can reasonably predict how many cells have been grown and how long before the support is saturated.

While cell growth can be monitored by visual inspection, microscopy, the rates of change in the growth parameters listed below also provide a means for monitoring cell growth:

(1) the medium pH differential across the support ($\Delta$pH), i.e., inlet pH versus outlet pH;
(2) the glucose consumption rate (GCR), i.e., the rate at which glucose must be added to maintain either an optimal or a given level;
(3) the dissolved oxygen (DO) differential across the support ($\Delta$DO), i.e., inlet DO versus outlet DO;
(4) the carbon dioxide ($CO_2$) demand (CDD), i.e., the rate at which $CO_2$ is needed to maintain either an optimal or a given pH; and
(5) the oxygen ($O_2$) consumption rate (OCR), i.e., the rate at which $O_2$ must be introduced into the medium to maintain either an optimal or a given level.

Of course, the more parameters monitored for rate of change and the greater the frequency of measuring, the better one can quantify the cell growth present on the support.

Certainly the ability of the present invention to grow cells is important, but it is not the whole story. The efficiency of any culture method/apparatus is based also on the ability to harvest the grown cells. The harvesting should be judged on quantity, percent yields, and quality, percent of uninjured cells which retain their reproductive ability.

The instant cell harvesting method is essentially a three phase process:

(1) removing soluble factors in the growth medium which can inhibit the ability of disassociating agents;
(2) treating the cells to be harvested with disassociating agents, i.e., reagents capable of disrupting cell-cell and cell-surface interactions, for a time sufficient to effect the desired degree of disruption; and
(3) exerting a shear force on the treated cells by circulating the liquid medium. An optional fourth phase may be separating the treated cells from the medium.

In the first phase, the soluble inhibiting factors must be removed from the medium. A preferred way is to add a quantity of a chelating agent such as calcium-/magnesium free-phosphate buffered saline (CMF-PBS). Of course, the amount added should be sufficient to tie up all of the inhibiting factors.

Next, the cells are treated with known disassociating agents. These agents serve to disrupt the attractive or binding forces which have developed both between cells and between cells and the support surface. Suitable agents include proteolytic enzymes and chelating chemicals. An about 0.1% solution of trypsin combined with an about 0.5 millimolar (mM) solution of ethylenediaminetetraacetic acid (EDTA) is preferred.

The disassociating treatment lasts for a time sufficient to disrupt essentially all cell-cell and cell-surface interaction. Thus a higher cell density requires more time than lower densities. An example of a preferred time for a given density would be about 30 minutes for a cell density of about $2.2 \times 10^5/cm^2$. Of course, during this time it is preferred that the medium does not circulate over the monolith support.

At the third phase, the cells are ready to be separated from the support surfaces. A shear force is put upon the cells by circulating the medium over the treated cells at a speed sufficient to dislodge them. Preferred flow speeds for the medium are from about 0.75 to about 6 cm/sec depending upon cell density and type. Special selection can also be based upon whether one wants as complete a removal as possible, a quantitative removal, or merely a partial removal, perhaps for sampling purposes. In any event, this phase lasts until the desired degree of separation is achieved.

One of the important attributes of the immobilized cell composite as used in a mass cell culture apparatus/process is the ability to provide cells with a sufficient exposure to vital nutrients throughout all the channels for their total length. This is accomplished in spite of the high cell density, high aspect ratios and small cross-sectional channel openings which characterize the instant composite. Important to this is the means for providing non-turbulent flow which is positioned about the support.

The means surrounding the support is designed and configured to ensure a laminar, non-turbulent flow of medium through the entire cross-section and length of the monolith. In a typical configuration, it is a close fitting jacket which sheaths the monolith, only exposing the channel ends. In some cases the jacket is segmented.

At the exposed portions the means is adapted and configured to smoothly transition the flowing medium into and out of the monolith. It narrows from the monolith diameter to that of the means for supplying the medium to the support. Preferably, a distributing means is placed in the transition area, in the flow itself. This means uniformly distributes the medium into all of the support channels. The main consideration is to essentially eliminate turbulent flow and provide an adequate medium flow throughout the cross-section of the monolith.

Various materials are suitable for the non-turbulent flow means, all being medium insoluble, and non-toxic to the cells being grown. Suitable compositions are glasses, ceramics, plastics, metals and other materials known to the art. Of course, the diversity of materials allows different construction methods.

A preferred example of forming a composite permits rapid assembly or disassembly. The means for ensuring non-turbulent flow is segmented in at least two pieces such that the segments can be easily separated, the monolith either quickly installed or replaced, and the segments rejoined in a sealed manner.

The following configuration would be typical. The monolith jacket is in two cylindrical pieces of identical configuration. Each has an inner diameter designed and configured to allow the insertion of the cylindrical support. At one end the segment is shaped to form a butt-flanged seal with another segment. At the other end it is adopted and dimensioned to secure an inserted monolith of suitable length from sliding about within the assembled composite, and also to provide a smooth transition means between the flow supply means and the monolith.

The composite is assembled by inserting the monolith inside one of the appropriately configured segments. The complementary segment is then slid over the exposed end of the monolith until the flanged segment ends meet. Finally, a clamp conventionally used in securing and sealing butted glass tubing is placed about the flanged ends and tightened. The unit is ready for sterilization and seeding.

Just as the composite non-turbulent flow means may be segmented for ease of construction and assembly, the support may also be. The support can be in the form of notched segments which are complementary. Each segment is designed to properly align with and orient to its adjacent segment. The important consideration is that the channels match up to allow a non-turbulent flow within the interior of the support as well as minimizing the number of orientation steps in the seeding stage. While this assembly may not be monolithic in the sense of a one-piece construction, it is monolithic in that the alignment and orientation of support growing surfaces is maintained through the joined segments.

The instantly disclosed cell culturing apparatus offer significant advantages over known cell culturing devices. The support configuration provides a relatively high cell-anchoring surface area within a reactor of manageable volume, yet still permits essentially unrestricted laminar flow of the fluid culture medium. This not only insures efficient supply of the medium to all cells, but also permits the rapid equilibration of nutrient medium to optimal conditions prior to recirculation.

In addition, increases in culture productivity can be obtained in a direct proportion to increases in support volume (at a constant surface area:volume ratio). In other words, scale-up of production is fairly simple and direct. This is not possible with known cell culturing systems based, for example, on roller bottle supports. Relatively large, high-output cell propagators can be made according to the present disclosure, without the increased labor costs, handling steps and risk of contamination which would occur in the scale-up of a roller bottle and microcarrier cell culturing operation.

Additional savings in labor and materials can be realized in providing automatic, continuous monitoring and adjusting of dissolved nutrients and gases needed for cell sustenance and/or growth. Instead of the medium being completely replaced at least once, as in typical roller bottle operations, the present apparatus can grow equivalent numbers of cells on less media than known culture systems. This is achieved with a combination of: a means for recapturing and/or storing the spent medium; a means for monitoring the degree of needed replenishment; a means for adjusting the medium to proper levels; and a means for recirculating the optimized medium. Preferably, this is all done automatically.

Further advantages in processing costs may be achieved in the recovery of cell products. With the present composite, anchored cells are always separated from the nutrient reservoir. If a desired product is released by the cells into the medium, it is easily recovered by being separated from the medium in the nutrient reservoir by conventional methods. By altering the reservoir quantity, the product concentration is proportionately altered. For example, a lowered volume of medium in the reservoir will result in high product concentrations. Neither microcarrier or suspended culture systems can provide this ability.

BRIEF DESCRIPTION OF THE DRAWINGS

The invention may be further understood by reference to the drawings, wherein.

BEST MODE FOR CARRYING OUT THE INVENTION

Before describing the best mode, it will be helpful to the reader to present a definition:

For present purposes, the aspect ratio is the ratio of the length of the monolith (measured parallel to the channels) to its largest cross-sectional dimension.

The Assembled Composite

In a preferred embodiment, the immobilized cell composite is an assembly of a support and a flow-providing means. The support for the immobilized cell composite is a monolith, shown in FIGS. 1 and 2, comprised of parallel channels (12) of substantially equal dimensions separated by common walls (14). This support constitutes a single unit of variable length and cross-sectional area, and is encased in a close-fitting jacket (16) whereby there can be laminar, non-turbulent flow of cell nutrient medium throughout all channels of the monolith. This provides the distinct advantage of uniform exposure of cells anchored to the channel walls to the nutrients in the medium a problem in the prior art.

Figure 6:
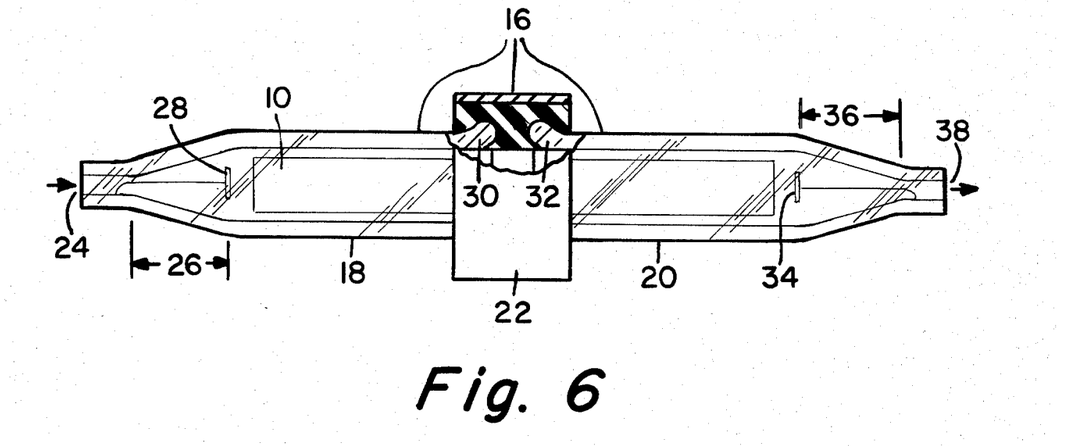
FIG. 6 is a side-elevational view in partial cross-section of an immobilized cell composite having a segmented non-turbulent flow means.

As set forth in FIG. 6, a preferred support assembly comprises a cylindrical monolith support (10) and a segmented means (16) for providing non-turbulent flow of culture medium into, through, and out of the support. In the illustrated assembly, the segmented means (16) comprises symmetrical glass jacket portions (18, 20) with a means (22) for securing them together.

Starting from the composite assembly inlet (24) and proceeding along the flow means (16) toward the outlet (38), the inlet glass jacket portion (18) has an opening (24) for allowing the introduction of medium into the assembly. Adjacent to the inlet is a flow-transition area (26). Frusto-conical in shape, this area adapts the cross-sectional area of the inlet to that of the support. Positioned at the support end of this area is a fritted disc (28). It is dimensioned and configured to distribute the flow of medium into all of the support channels (12).

From the transition area (26) the jacket portion (18) has a cylindrical form which sleeves the support. The sleeve (30) end of the inlet jacket portion (18) is adapted to butt the complementary end (32) of an identical outlet glass jacket portion (20) when about the middle of the sleeved support. The outlet portion is identical to the inlet also having a disc (34), a flow-transition area (36), and an outlet opening (38). These jacket portions are secured together by conventional means such as a glass tubing clamp (22).

Figures 9, 10:
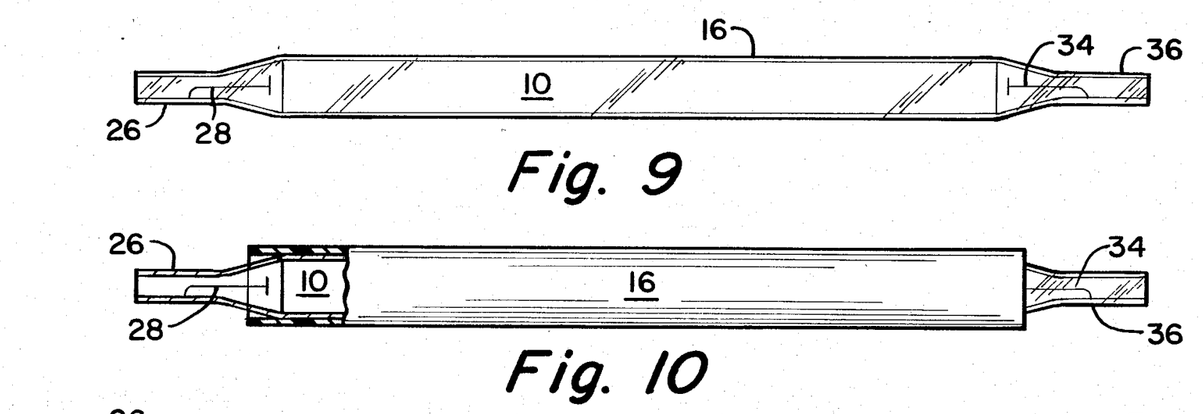
FIG. 9 is a side elevational view of a glass-encapsulated monolith support assembly.
FIG. 10 is a side elevational view in partial cross-section of a monolith support and transition end caps inserted into a shrinkable plastic sleeve.

Alternate assemblies can be made. For example, as shown in FIG. 10, in the case of heat-shrinkable materials known to the art, the monolith (10) can be inserted within a selected piece complementary in shape (at least when shrunk). The pre-shrunk piece (16) is slightly larger than the support so as to allow insertion. The transition portions (26, 36) of the non-turbulent flow means have flow distributors (28, 34) and are separate from the main body which surrounds the support. They are made of non-heat-shrinkable materials so that when the main body shrinks about both the support and the ends, a non-turbulent flow means is formed.

To assemble the composite, the support is inserted into the pre-shrunk, plastic shape. Then the ends are inserted in alignment with the channel openings. Heat is applied and, as shown in FIG. 11, the material shrinks about the support (10) and the ends (26) forming the means whereby a non-turbulent flow sweeps through the monolith channels and past the anchored cells.

Figures 11, 12:
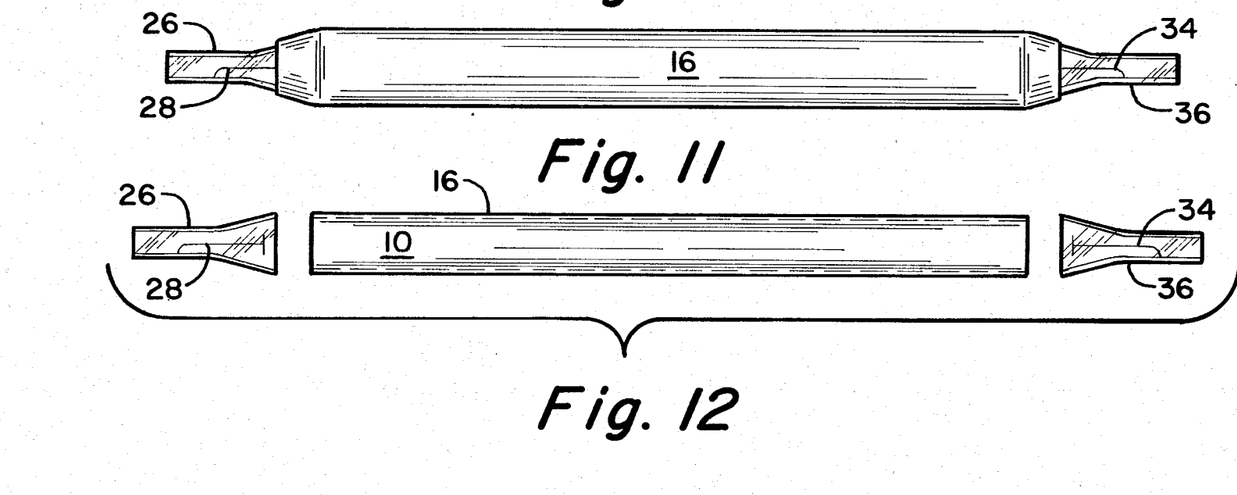
FIG. 11 is a side elevational view of the assembly of FIG. 10 after the sleeve has been shrunk.
FIG. 12 is a elevational exploded view of a glaze-encapsulated monolith support.

Another way to fabricate the composite is shown in FIG. 12. The exterior of the monolith (10) is coated with known glazes (16), only leaving the channel ends open. The monolith can be either sprayed with or dipped in the selected glazing material. After being applied, the monolith is subjected to known, suitable techniques for fixing the glaze, e.g., heat treatment. As in the case of the shrinkable plastic composites, transition end portions (26, 36) with flow distributors (28, 34) may be needed. They may be joined to the monolith at the channel ends by conventional means to form the assembly.

For example, a ceramic honeycomb formulation of alumina and zircon can be extruded into a monolith support which yields 63.9 wt % mullite+36.1 wt % zirconia after firing at 1600° C. This material has a coefficient of thermal expansion of $58 \times 10(-7)/C$, in the range room temperature to 1000° C. It is encapsulated with a glaze which closely matched it in expansion and preferably slightly lower so that the glaze is put in compression. A suitable composition would be 45.2% silica, 29.6% PbO, 8.0% boric oxide, 7.1% CaO, 5.7% alumina, 2.3% soda, 0.9% potassia, 0.7% zirconia, 0.2% CdO.

After melting, the composition is reduced to a fine powder, about 325 mesh. It is applied to the honeycomb surface in the form of a suspension in water with a small amount of organic binder. After drying at 100° C., the coated support is fired at 1090° C. for 1 hour in an air atmosphere. The result is a good fitting glazed honeycomb whose surface is impervious to liquids.

A third method for assembling the composite uses a glass casing. The monolith support is placed into a glass material that is complementary in shape, but slightly larger than the support. The channel ends are matched with openings in the casing.

For example, a cylindrical monolith is fitted inside glass tubing whose inner diameter is slightly larger than the outer diameter of the support. In selecting the glass, consideration should be given to either matching or closely approaching the coefficients of thermal expansion of the support and the glass. This will reduce the stresses on both the glass and the support during the next step.

As illustrated in FIG. 9, the glass is then heat-shrunk about the monolith (10) by conventional means. For example, the glass (16) is axially rotated while being heated for its entire length. To preclude the use of separate transition end portions (26, 36), the heated glass ends may be either enlarged or reduced to a desired diameter while in a workable state. Flow distributors (28, 34) may be placed inside the transition areas.

The above composites have differences in compositions, elements, and methods of assembly. However, they all have the novel, previously described monolith support, and a means about the support which transitions flow into, through, and out of in such a manner that cells anchored to the support are presented with a laminar, non-turbulent flow of medium.

The Monolith Support

Figures 4, 5:
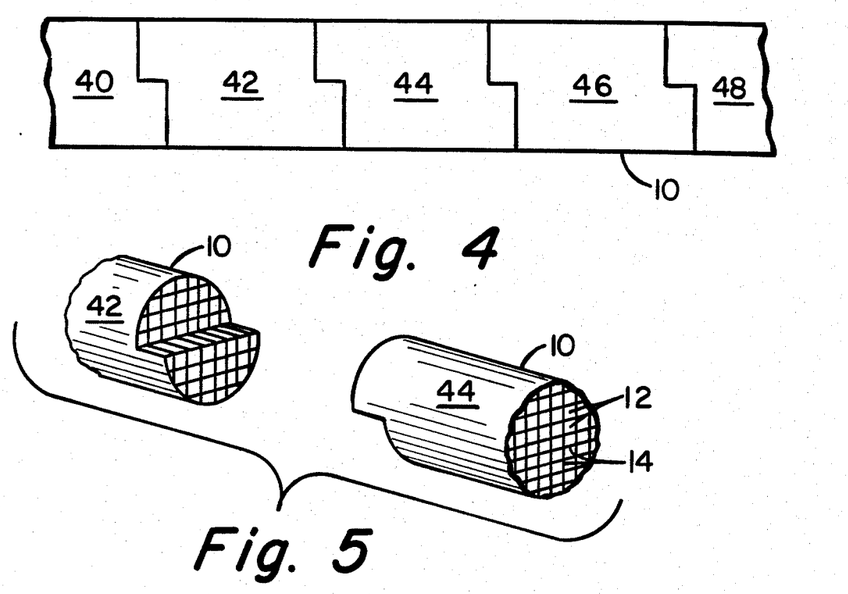
FIG. 4 is an elevational view of a segmented monolith support.
FIG. 5 is an exploded view of the support in FIG. 4.

It should be noted that the monolith support can also be segmented (40-48), see FIGS. 4 and 5. Each segment is designed to properly align with and orient to its adjacent segment. The important consideration is that the channels match up to allow a non-turbulent flow within the interior of the support as well as minimizing the number of orientation steps in the seeding stage. FIG. 5 shows an exploded view of two segments and how they match up. While this assembly may not be monolithic in the sense of a one-piece construction, it is monolithic in that the alignment and orientation of support growing surfaces is maintained throughout the joined segments.

The shape of the channels (12) forming the support structure is not critical. Square, round, triangular and other shapes are essentially equivalent for the purpose of culturing cells in accordance with this invention. However, the size of the channels is an important variable affecting the suitability of the support. Excessively large channels reduce the surface area to volume ratio of the support and thus do not efficiently utilize the volume of culture medium available. On the other hand, excessively small channels restrict the medium flow such that it is difficult to maintain optimal pH and dissolved gas levels when the medium is adjacent to the cells.

The aspect ratio of the monolith is not a critical factor for cell growth provided that the maximum flow rate of medium through the channels can provide adequate nutrient levels to cells substantially throughout the channel length, as well as remove waste by-products such that maximum waste levels are avoided. Aspect ratios in the range of about 1:100 are suitable for the range of flow rates possible with the present cell culture supports.

The composition for the channel walls of the monolith, be it organic or inorganic, should have the following characteristics: (1) be substantially medium-insoluble and non-toxic to the cell population being cultured; (2) be a surface to which the animal or plant tissue cell type of interest will anchor; and (3) be one which can be bonded into a material of sufficient strength to form a channel wall.

Examples of compatible materials include silica, fritted borosilicate glass, mullite ($3Al_2O_3 \cdot 2SiO_2$), cordierite ($2MgO \cdot 2Al_2O_3 \cdot 5SiO_2$), manganese cordierite ($\beta\text{-}aMgO \cdot aMnO \cdot 2Al_2O_3 \cdot 5SiO_2$), zircon ($ZrO_2 \cdot SiO_2$), mica, and spodumene ($Li_2O \cdot Al_2O_3 \cdot 4SiO_2$). Alumina ($Al_2O_3$) and titania ($TiO_2$) were also found to be suitable, provided they were thoroughly washed prior to use. Of course, combinations of two or more of the compatible materials disclosed above would also be suitable.

The Cells

The selection of a material for the support will depend in part on the tissue cells to be cultured. Some tissue/support material combinations provide results comparable to or superior to those obtained with plastic roller bottles, while others can be somewhat less effective. Table I, below, sets forth examples of some specific cell types which can be cultured using composites provided according to the invention. Included are an identification of: the cell types employed; the characteristic or typical use of the cells in tissue culture; and some preferred support materials exhibiting culture compatibility with the cells.

TABLE I
Cell Identification

| | |
|---|---|
| | Cell Type/Source |
| WI-38 | diploid fibroblast/human lung |
| HeLa | transformed human tumor |
| BHK-21 | fibroblast/hamster kidney |
| CEF Primary | fibroblast/chick embryo |
| Vero | epithelial/monkey kidney |
| HFS | fibroblast/human foreskin |
| RPMI-1788 | lymphocyte/human peripheral blood |
| RTG-2 | fibroblast/rainbow trout gonad |
| *Aedes albopictus* | epithelial/mosquito larva |
| Primary monkey | epithelical/Rhesus kidney |
| | Character/Use |
| WI-38 | vaccine production |
| HeLa | tumor studies |
| BHK-21 | virus production |
| CEF Primary | veterinary vaccines |
| Vero | virus production |
| HFS | interferon production |
| RPMI-1788 | immunoglobulin secretion |
| RTG-2 | fish virus studies |
| *Aedes albopictus* | arbovirus prop. |
| Primary monkey | vaccines, virology |

The Cell Culture System

Optimal use of the instant monolith support is achieved in a system designed to promote either maximum cell growth or cell sustenance with minimum supplies. An adequate presence of nutrients must be made available continuously to growing cells. Wastes which interfere with growth also should be removed.

Figures 1, 2, 3:
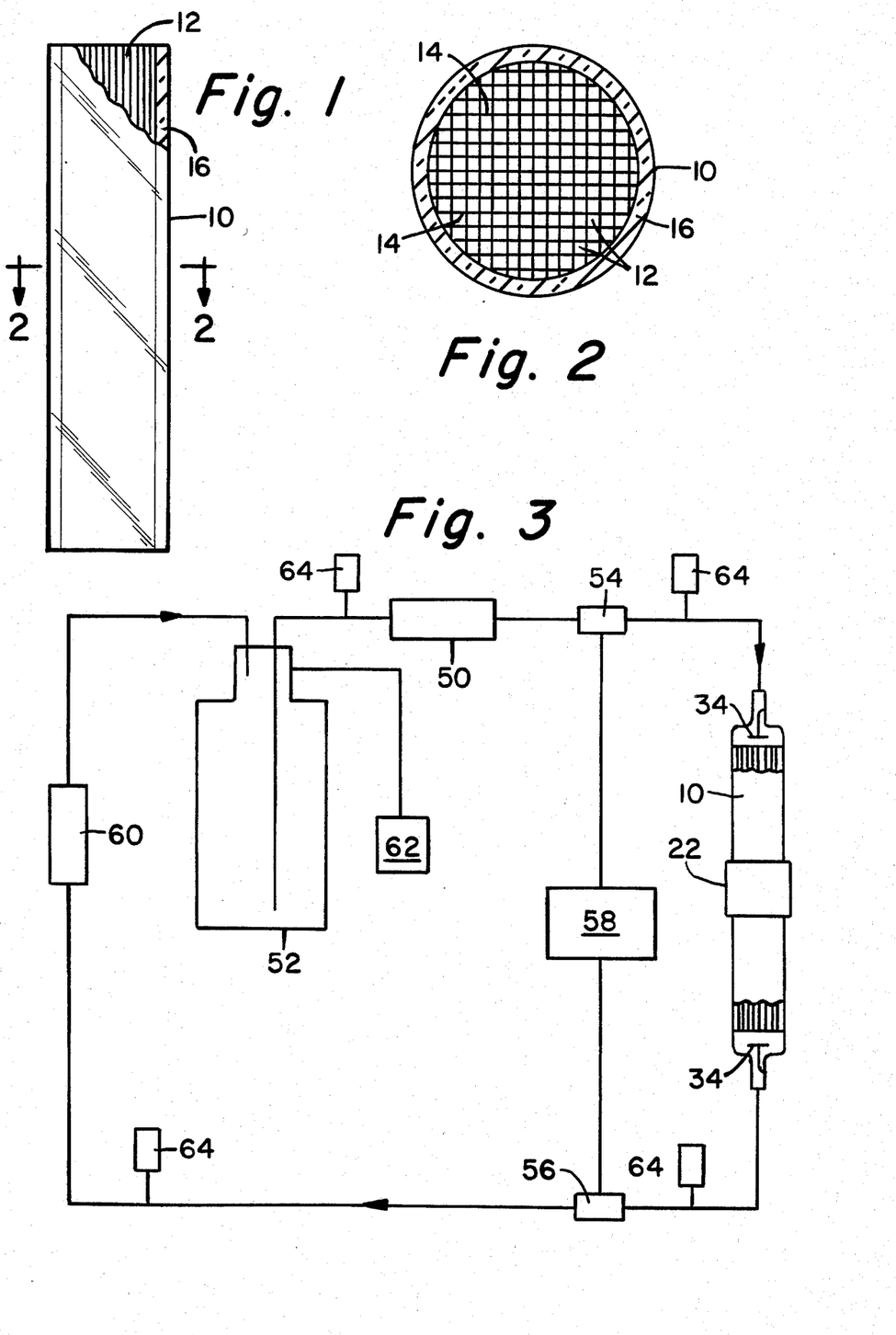
FIG. 1 is an elevated view in partial cross-section of a monolith support.
FIG. 2 is a cross-sectional view of a monolith support.
FIG. 3 is a schematic diagram of a cell culture apparatus using a monolith support composite.

FIG. 3 is a schematic of a preferred culture system using a monolith support. A medium containing the nutrients suitable for either cell growth or sustenance is flowed over the growing surfaces of the monolith support (10) by means of a pump (50) which pulls the fluid from a reservoir (52), into, then through the support. Optionally, multiple supports can be run simultaneously if they are manifolded together in a parallel manner. The medium and the support are maintained at an optimal temperature by conventional means.

As the medium is recirculated into and out of the support, it encounters continuous, automatic sensors (54, 56) for measuring pH, glucose, dissolved $CO_2$ and dissolved $O_2$ levels. These sensors constantly report back to a central, process-controller computer (58) which, in turn controls the medium flow (pump 50) as well as its replenishment. More particularly, the controller operates mechanisms, such as a gas permeator (60) and buffer and glucose solution reservoirs (62) with pumps (80), which can restore depletion in the spent medium. Fractions of medium are sampled and additions made at collector ports (64).

Figure 7:
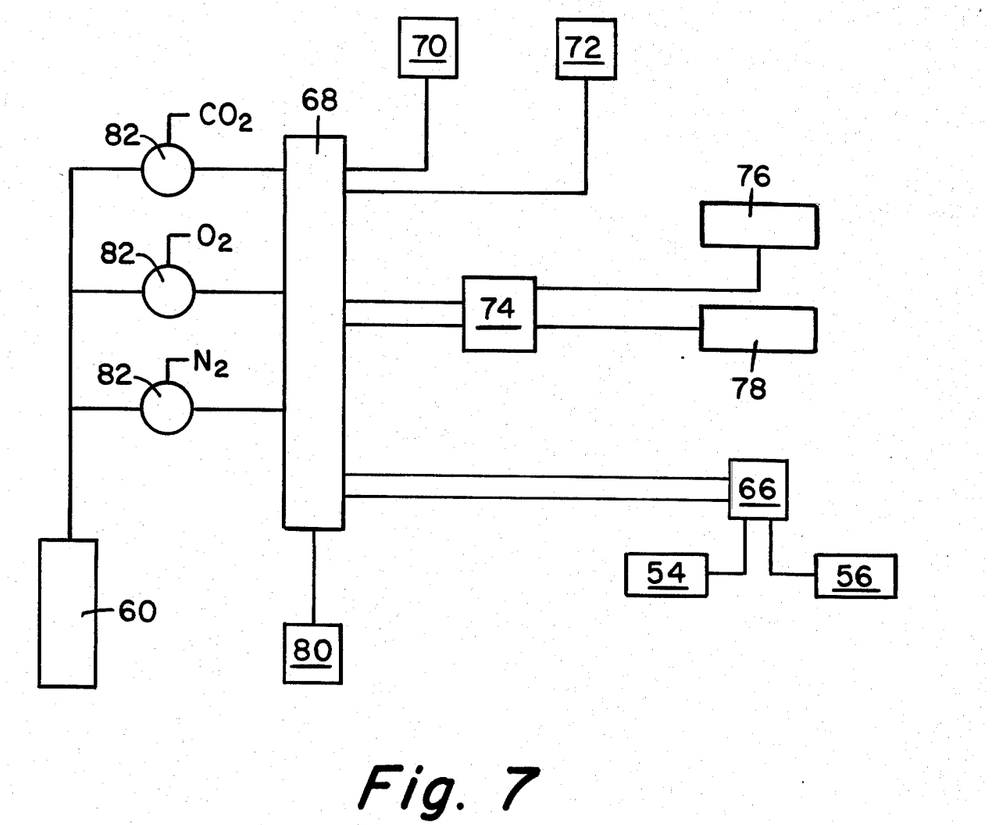
FIG. 7 is a schematic diagram of the automatic and continuous process control system as used in a cell culture apparatus.

A more detailed illustration of the automatic system control may be seen in FIG. 7. Here probes (54 and 56) sense pH, glucose, dissolved $CO_2$ and $O_2$ levels. Alternatively amino acid and cell metabolite concentrations could be measured. This information is changed into electrical signals which are first strengthened by amplifiers (66) then transmitted to a combination automatic/manual interface (68). Panel meters (70) are fed by the interface for instantaneous read-out. If manual operation is desired, a technician can monitor the panel read-out and adjust manual controls (72) for glucose, pH, dissolved $CO_2$, $O_2$, and dissolved nitrogen ($N_2$).

If automatic control is desired, the sensor data is transmitted into a central computer (74) having sufficient memory and calculating power to quickly drive the system controls. A Hewlett-Packard HP9915 would be suitable. As it receives the condition of the medium entering and exiting the support, the computer calculates the necessary change which must be made to the medium in order to restore it before it is recirculated into the support. These calculations are constantly updated and are based on a software program that would be conventional to skilled artisans.

Almost simultaneously with the calculations, the computer displays the sensor data, the system needs, and the actions necessary to correct these needs on a plotter (76) and/or video terminal (78). At the same time, it sends signals back to the interface where they are relayed to the appropriate servo mechanism. For example, pumps to feed buffer and glucose solutions (80) may be activated for set times based on system need, pump output, and solution concentrations. In addition, gas mass flow controllers (82) may be activated to increase or decrease the amount of $O_2$, $CO_2$, and $N_2$ being directed into the gas permeator (60), or optionally directed straight into the reservoir (52) at a rate sufficient to avoid foaming (not shown).

The net effect of this control array is a means wherein the medium needs may be automatically and continuously monitored and the appropriate replenishment steps automatically and continuously performed. The labor and material savings is significant.

Figure 8:
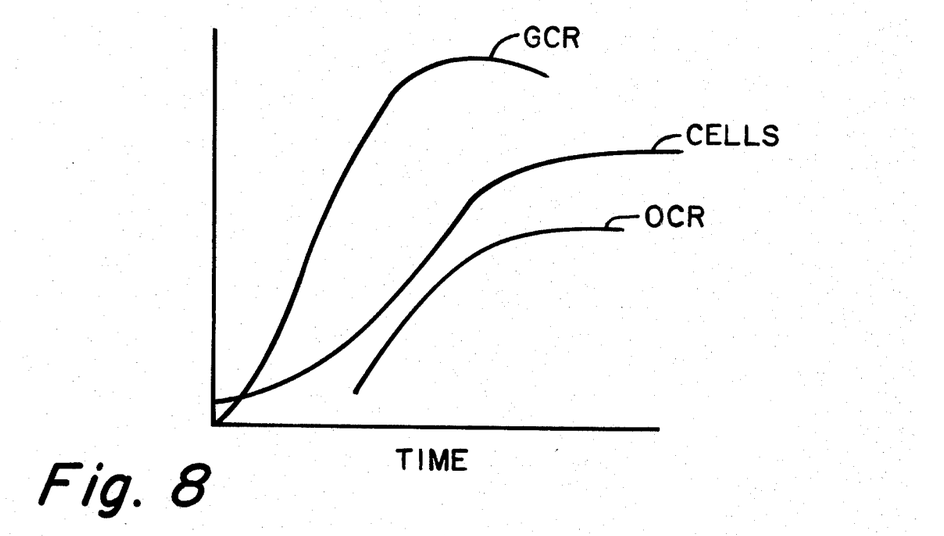
FIG. 8 is a pictorial diagram showing the interrelationship of control parameters to cell growth.

It should be noted that in practice a method of projecting a cell growth curve or profile which helped the system operator was disclosed. It has been discovered that the rate of change in the OCR and the GCR are related to saturation of the support with cells, i.e., a plateau in cell number. This is shown in FIG. 8. Thus, a monitoring of the OCR and GCR will reveal cell saturation.

EXAMPLE 1

The following detailed example sets forth the preparation and use of a cell culture composite in accordance with the invention.

The Support

A monolithic ceramic support in the form of a honeycomb structure consisting of a multiplicity of parallel channels of square cross-section is selected for use as the culturing support. This monolith is composed of cordierite ($2MgO \cdot 2Al_2O_3 \cdot 5SiO_2$) and is in the form of a cylinder about 2 cm in diameter and 6 cm in length. It has about 300 channels per square inch of cross-sectional area traversing the length of the structure.

A suitable assembly for efficiently utilizing the support is to surround the support in a tight-fitting cylindrical jacket which will transition the medium into, through, and away from the support in a non-turbulent manner. It is prepared for use by known washing and sterilization techniques.

The Cells

The cells to be grown on the monolith are taken from a subculture of human foreskin fibroblasts (HFF). The cells are separated from the subculture using a buffered proteolytic enzyme solution (0.25% trypsin in calcium/magnesium free phosphate buffered saline [CMF-PBS] at pH 7.4) after thorough rinsing of the subculture with CMF-PBS to remove all serum-containing growth medium. The enzyme solution is applied to the subculture in a volume of about 0.5 ml per 25 $cm^2$ of culture surface area, incubated at 37° C. for 10 minutes, and the separated cells and solution diluted to at least double volume by the addition of cold (4° C.) growth medium containing 10% fetal bovine serum (FBS).

The cells are then centrifigally separated from the suspension and resuspended in fresh cold (4° C.) growth medium prior to use. This medium is used for all cell preparation and culturing, and is referred to as Hanks minimum essential medium (MEM-Hanks) containing L-glutamine and NEAA, supplemented with Hepes buffer (20 mM), 0.035 gm/l $NaHCO_3$, 100 µg/ml Garamycin, and 10% FBS.

Seeding the Support

The sterilized monolith is seeded with HFF cells from a cell suspension containing $1.25 \times 10^5$ cells/ml of the suspending medium. The medium does not require serum because it is simply a vehicle for transporting the cells into the monolith for attachment to the cell walls.

To achieve uniform seeding, the monolith which has previously been flooded with circulating serum-free growth medium is positioned horizontally and connected to a flask containing the seeding suspension using a length of silicone tubing, the monolith being so oriented that one of the four sets of channel side walls is horizontally disposed. The serum-free medium present in the monolith is then displaced by pumping into the monolith an equal volume of the cell suspension medium.

After a 15-minute interval during which gravitational settling of the cells onto the horizontal channel walls is permitted to occur, the monolith is rotated 90° about the cylinder axis and the seeding process is repeated for a second set of channel walls. This process is repeated until all four sides of the square channels have been seeded.

Culturing the Seeded Cells

After seeding has been completed, the serum-free medium in the monolith is replaced by the MEM-Hanks growth medium containing 10% FBS and the monolith is allowed to stand for several hours. Thereafter, slow recirculation of the growth medium through the monolith is commenced, which during the early lag phase of cell growth on the monolith is at the rate of 0.25 cm/hr. This flow rate can be increased to between 0.5-40 cm/min. during the rapid growth phase of the cell culture. Continuous monitoring of growth medium pH and replacement of the recirculating growth medium on a periodic basis maintain optimum growth conditions for the cells.

Comparison

The effectiveness of the monolith as a tissue cell culture support can be established by comparative testing with plastic support media such as roller bottle or microcarrier supports. Indicators of support performance are: the duration of the lag phase prior to the onset of rapid cell growth; the rate of cell growth during the rapid growth phase of the culture; and maximum cell density attainable on the support.

Quantification of these variables is conveniently accomplished by assays of cellular protein present on each support type at various times after innoculation. It is known and accepted by those skilled in the art to convert cell protein/$cm^2$ of support surface area to cells/$cm^2$ of support surface area. A conversion basis of $2.6 \times 10^6$ cells per mg of protein present may be used.

Techniques for protein assay are well known, one suitable technique involving the elution of cell protein from the support using NaOH and the quantitative determination of protein present in the eluent via infrared absorption at 750 nm using a folin phenol reagent. This determination is more fully described by O. H. Lowry et al. in "Protein Measurement with the Folin Phenol Reagent", *J. Biol. Chem.*, 193, pages 265-275 (1951) and reference may be made thereto for detailed information on the procedure.

A comparison of culture support characteristics between a number of presently disclosed cordierite monolith supports, plastic roller bottle supports, and microbead carrier supports of the type commonly used in the prior art has been conducted. All of the supports were initially innoculated with a suspension of HFF cells at a concentration of about $1.25 \times 10^4/cm^2$. The roller bottles and microcarrier were operated according to known and accepted practices.

The maximum cell yields obtained with the three supports are tabulated below:

TABLE II

| Support Type | Maximum Cell Yields<br>Maximum Cells/$cm^2$ |
|---|---|
| Plasma-treated polystyrene (Corning) | $6.2 \times 10^4$ (6 determinations) |
| Derivated sepharose beads (Pharmacia) | $6.8 \times 10^4$ (3 determinations) |
| Cordierite monolith support | $13.7 \times 19^4$ (2 determinations) |

While the post-seeding and rapid growth phases for the three different culture supports are quite similar, the density of cell population attainable on the monolith supports was at least 2-fold higher in all cases than was attainable on the plastic supports. This clearly illustrated the ability of the monolith for culturing very dense populations of cells.

EXAMPLE 2

This example demonstrates the superior performance of the composite in conjunction with the presently disclosed cell culture apparatus and process.

Two culture runs were performed with an apparatus as shown in FIGS. 6 and 7. Vero TM cells, an epithelial-monkey kidney cell line commercially available from the American Type Culture Collection of Rockville, Md., were seeded onto roller bottle controls and a monolith support having a cell growth surface area equivalent to fifty conventional roller bottles (50 R.B.E.) at the rate of 20-25 million cells per RBE.

For eight days the controls and the support were fed a Delbecco's Minimum Essential (DME) nutrient growth medium containing 4.5 grams of glucose per liter. The support culture system was operated as previously described, while the roller bottles runs were done in a conventional manner. After this time, the cell growth was harvested with a trypsin-EDTA solution according to the preferred methods previously described for use with the apparatus of FIG. 6. The cell yields were as follows:

50 RBE support run No. 1: $5.55 \times 10^8$ cells per RBE
50 RBE support run No. 2: $7.85 \times 10^8$ cells per RBE
Roller bottle control runs: 2.00 to $4.00 \times 10^8$ cells per RBE.

EXAMPLE 3

As in Example 2, a Vero cell culture was run on a monolith support using the above seeding, culturing and harvesting techniques. However, in this case the support had a 220 RBE rating. Again, the cells were harvested after 8 days with the following results:

220 RBE support run: $5.00 \times 10^8$ cells per RBE
roller bottle control runs: $2.00-4.00 \times 10^8$ cells per RBE.

Having described the invention with particular reference to preferred form, it will be obvious to those skilled in the art to which the invention pertain, that, after understanding the invention, various changes and modifications may be made without departing from the spirit and scope of the invention as defined by the appended claims.

We claim:

1. An immobilized cell composite comprising:
   (a) a high surface area monolithic support having an inlet and an outlet end, a multiplicity of mutually parallel channels passing therethrough, the channels having walls formed of a medium-insoluble, non-toxic, composition and the support having at least about 20 channels per square inch of cross-sectional area; and
   (b) a population of plant or animal tissue cells anchored to the porous channel walls.

2. A composite in accordance with claim 1 wherein the dimensions of the channels and channel walls are such that the support contains about 100–1000 channels per square inch of cross-sectional area.

3. A composite in accordance with claim 1 wherein the support has an aspect ratio in the range of about 1:100.

4. A composite in accordance with claim 2 wherein the support contains at least 400 channels per square inch.

5. A composite in accordance with claim 4 wherein the channels have a square cross-sectional area.

6. A composite in accordance with claim 1 wherein the channel walls are formed of a sintered, porous ceramic material selected from the group consisting of cordierite, alumina, silica, titania, mullite, zircon spodumene, mica, and combinations thereof.

7. A composite in accordance with claim 6 wherein the porous ceramic material is cordierite.

8. A composite in accordance with claim 1 wherein the cell population is derived from plant tissue.

9. A composite in accordance with claim 1 wherein the cell population is derived from animal tissue.

10. A composite in accordance with claim 9 wherein the cell population is a lymphocyte, epithelial or fibroblast type.

11. A composite in accordance with claim 10 wherein the tissue source is human.

12. A process for culturing plant or animal tissue cells wherein the cells are anchored to a monolithic medium-insoluble, non-toxic support and a cell nutrient medium is flowed past the cells, characterized in that
    (a) the support consists of a monolith having a multiplicity of parallel channels passing therethrough and an inlet and outlet end;
    (b) the channels have walls suitable for cell anchoring; and
    (c) the support has at least about 20 channels per square inch of cross-sectional area.

13. The process recited in claim 12 wherein the cell nutrient medium is constantly monitored for nutrient and metabolite levels and adjustments are constantly made to the medium to optimize the nutrient levels.

14. The process recited in claim 13 wherein the monitored and optimized nutrient levels are the pH of the medium, dissolved oxygen level, dissolved carbon dioxide level, and glucose concentration.

15. A process in accordance with claim 12 wherein the channel walls are formed of a composition selected from the group consisting of cordierite, alumina, silica, titania, mullite, zircon, spodumene, mica, and combinations thereof.

16. A process in accordance with claim 15 wherein the support has at least about 100–1000 channels per square inch of cross-sectional area.

17. A process in accordance with claim 16 wherein the cell population is of lymphocyte, epithelial, or fibroblast type.

18. A process in accordance with claim 16 wherein the medium is flowed through the channels at a linear flow velocity not exceeding about 36 cm/min.

* * * * *